United States Patent [19]
Choi et al.

[11] Patent Number: 5,964,729
[45] Date of Patent: Oct. 12, 1999

[54] PERFORATING DEVICE FOR DERMAL ADMINISTRATION

[75] Inventors: Sang Bae Choi; Kwang Kyun Jang, both of Kyungki-Do, Rep. of Korea

[73] Assignee: Samsung Electro-Mechanics Co., Ltd., Kyungki-Do, Rep. of Korea

[21] Appl. No.: 08/937,582

[22] Filed: Sep. 29, 1997

Related U.S. Application Data

[63] Continuation of application No. 08/450,950, May 23, 1995, abandoned.

[30] Foreign Application Priority Data

May 23, 1994 [KR] Rep. of Korea ............... 94-11248
May 23, 1994 [KR] Rep. of Korea ............... 94-11249
May 23, 1994 [KR] Rep. of Korea ............... 94-11252
May 23, 1994 [KR] Rep. of Korea ............... 94-11524

[51] Int. Cl.$^6$ ................................. A61B 17/20
[52] U.S. Cl. ...................... 604/47; 606/183; 606/186
[58] Field of Search .............................. 606/186, 183

[56] References Cited

U.S. PATENT DOCUMENTS 2,189,957  2/1940  Lundblad ........................... 30/307
2,471,763  3/1949  Merrick ............................. 30/306
3,918,449  11/1975 Pistor ............................... 128/218 R
4,483,348  11/1984 Sher ................................. 128/743
5,139,029  8/1992  Fishman et al. .................... 128/743

FOREIGN PATENT DOCUMENTS 92-2264  3/1992  Rep. of Korea .

Primary Examiner—Wynn Wood Coggins
Assistant Examiner—Deborah Blyveis
Attorney, Agent, or Firm—Lowe Hauptman Gopstein Gilman & Berner

[57] ABSTRACT

A perforating device for dermal administration of medicine is disclosed. The device includes skin perforating members provided with a plurality of needles and received in a casing. The skin perforating members have alternately arranged needle discs and spacer discs which easily and evenly perforates the skin to a depth, suitable for dermal administration of medicine, by simply rolling the assembly on the skin. The device also includes a biasing mechanism for elastically vertically moving the assembly during skin perforating and thereby preventing the skin perforating members from excessively perforating the skin. The device informs the user of the excessive pressure of the assembly and thereby preventing possible skin damage.

16 Claims, 11 Drawing Sheets a continuation of application Ser. No.
08/450,950 filed May 23, 1995, now abandoned.

BACKGROUND OF THE INVENTION

1. Field of the Invention

The present invention relates in general to a device for forming thousands of incisions on the skin for dermal administration of a pharmaceutically acceptable composition liquid or gel medicine, and more particularly, to a device for perforating the skin by rolling a needle assembly, having a plurality of needles, and thereby letting the liquid or gel medicine deeply infiltrate into the skin through the incisions when applying the medicine to the perforated skin.

2. Description of the Prior Art

Insulin is noted to be an efficacious medicine for, in particular, diabetics. However, insulin is a macro molecule having a molecular weight not less than 6000 so that the insulin scarcely infiltrates through the epidermis even when changing the skin characteristics using a chemical solvent. In addition, since insulin, a peptide, is a hydrophilic molecule, it does not have good affinity for the hydrophobic epidermis. In this regard, it has been noted that the insulin by itself cannot penetrate the epidermis and that the skin should be additionally treated when administering the insulin through the skin.

Human skin comprises an outer layer or the epidermis and an inner layer or the endodermis. The epidermis, comprises 20% fat and 40% protein and has a thickness not less than 0.1 mm. Thus, the epidermis barely allows the medicine to infiltrate.

The epidermis comprises protein segments surrounded by fat so that the epidermis has a hydrophobic property. In comparison with the epidermis and the endodermis, both having a water content of at least 70%, the epidermis has a relatively lower water content of about 40%. With the lower water content, the epidermis has a high electric resistance and functions as a protector for protecting the endodermis from outside stimulation such as thermal stimulation.

In the prior art, dermal administration of insulin is generally classified into three types, that is, an ointment type administration, a patch type administration and a spray type administration. Of the above three types, the patch type dermal administration of insulin has been recently studied with much interest.

Korean Patent Publication No. 92-2264 discloses an example of a patch type instrument for dermal administration of insulin. As shown in FIG. 1, the patch type instrument has an insulin solvent reservoir 1 and a high molecular carrier 2. The carrier 2 is evenly applied with insulin powder and has a water-swelling property. The above instrument also has a skin needle carrier 3 which will be swollen by the insulin solvent discharged from the reservoir 1 after attaching the instrument to the skin. A plurality of needles 4 are in a fixed, vertical arrangement in the carrier 3 and will come into contact with the skin when attaching the instrument to the skin. The instrument further includes an electrode 5 for sending current to the reservoir 1 and to the skin, the electrode 5 being arranged in the top section of the reservoir 1.

When using the above patch type instrument for dermal administration, the instrument is attached to the skin such that the needles 4 of the needle carrier 3 come into contact with the skin and form incisions in the epidermis. In this case, the perforations, or the insulin passages which are formed in the epidermis by the needles 4, are temporarily closed due to swelling of the skin. When the electrode 5 is applied with current, DC or ripple current, the ionized insulin and the solvent move to the opposed electrode. At this time, the hydrophilic protein and the polypeptides of the skin are arranged in parallel toward the anode and shrink so that the incisions in the epidermis open. Therefore, the insulin passes the epidermis through the incisions and, thereafter, infiltrates through the endodermis to be transferred to the capillary vessels.

In the above instrument, use of the needles 4 is for perforating only the epidermis having a thickness not less than 0.1 mm and letting the insulin be easily transferred to the capillary vessels through the epidermis, the epidermis and the endodermis and thereby increasing the medicating amount of the delivered insulin.

The above instrument has tens or hundreds of needles fixedly held by the water swelling carrier, the carrier being swollen by the insulin solvent discharged from the reservoir. However, it is very difficult to produce 50–400 $\mu$m diameter needles. In addition, as the carrier should be swollen by the insulin solvent discharged from the reservoir, the carrier made of water-swelling material increases the cost.

As the needle carrier and the insulin solvent reservoir are assembled into a set, the instrument should be discarded after one use. The instrument is thus wasteful of material and expensive.

Another problem of the above instrument resides in that the instrument merely has tons or hundreds of needles even though the instrument needs to be provided with thousands of needles for more rapid administration of insulin. Due to the shortage of needles, the amount of insulin solvent transferred to the capillary vessels through the skin for a unit time is insufficient so that diabetics must attache the instrument to the skin for a long time, enduring pain caused by needle perforation and discomfort from the uncomfortable motion caused by the instrument attached to the skin.

SUMMARY OF THE INVENTION

It is, therefore, an object of the present invention to provide a perforating device for dermal administration of a pharmaceutically acceptable composition in which the above problems can be overcome and which easily forms thousands of incisions on the skin by simply rolling a needle assembly on the skin and is produced separately from a patch.

It is another object of the present invention to provide a perforating device for dermal administration which controls the compressed state of the needles by elastically moving up and down the needle assembly and thereby scarcely generating skin damage during perforation.

It is a further object of the present invention to provide a perforating device for dermal administration which gives an alarm of excessive pressure on the needles and thereby preventing possible damage of the skin during perforation.

According to a first embodiment of the present invention, there is provided a perforating device for dermal administration comprising:

a casing having opposed shaft holes in its opposed bottom sides;

a bearing means set in each of said shaft holes of the casing; and perforating roller means having a plurality of perforating needles on its outer surface and a center rotating shaft, said roller means being rotatably supported, at the opposed side ends of the center rotating shaft, by the bearing means such that the roller means partially projects out of the bottom of the casing.

According to a second embodiment of the present invention, there is provided a perforating device for dermal administration comprising:

a casing having opposed steps in its opposed bottom sides;

a moving unit received in said casing such that it is elastically vertically movable in the casing, the bottom of said moving unit being seated on the opposed steps of the casing;

means for biasing the moving unit to make the moving unit elasticlly vertically move in the casing, said biasing means being interposed between the moving unit and the casing; and perforating roller means having a plurality of perforating needles on its outer surface and a center rotating shaft, said roller means being rotatably supported, at the opposed side ends of the center rotating shaft, by the moving unit such that the roller means partially projects out of the bottom of the casing.

In the above embodiment, it is desirable that the biasing means is a coil spring or a plate spring held on the center of the moving unit.

According to a third embodiment of the present invention, there is provided a perforating device for dermal administration comprising:

a casing having opposed steps in its opposed bottom sides;

a pair of moving units received in said casing such that the moving units are elastically vertically movable in the casing, each of said moving units having a spring holder and a bearing body;

means for biasing the moving units to make the moving units elastically vertically move in the casing, said biasing means being interposed between the spring holders of the moving units and the casing; and perforating roller means having a plurality of perforating needles on its outer surface and a center rotating shaft, said roller means being seated on the opposed steps of the casing and rotatably supported, at the opposed side ends of the center rotating shaft, by the bearing bodies of the moving units such that the roller means partially projects out of the bottom of the casing.

In the above embodiment, it is desirable that the biasing means is a coil spring or a plate spring held on the center of a pair of the moving unit.

According to a fourth embodiment of the present invention, there is provided a perforating device for dermal administration comprising:

a casing having opposed steps in its opposed bottom sides and a partition for dividing the inside of the casing into top and bottom chambers;

a moving unit receifed in said bottom chamber of the casing such that the moving unit is elastically vertically movable in the casing, the bottom of said moving unit being seated on the opposed steps of the casing;

means for biasing the moving unit to make the moving unit elastically vertically move in the casing, said biasing means being interposed between the moving unit and the casing;

perforating roller means having a plurality of perforating needles on its outer surface and a center rotating shaft, said roller means being rotating shaft, by the moving unit such that the roller means partially projects out of the bottom of the casing; and means for sensing and displaying vertical movement of said moving unit, said sensing and displaying means being placed in said top chamber of the casing.

According to a fifth embodiment of the present invention, there is provided a perforating device for dermal administration comprising:

a casing having opposed steps in its opposed bottom sides and a partition for dividing the inside of the casing into top and bottom chambers, said partition having a pair of holes;

a pair of moving units received in said bottom chamber of the casing such that the moving units are elastically vertically movable in the casing under the guide of the holes of the partition, each of said moving units having a spring holder and a bearing body;

means for biasing the moving units to make the moving units elastically vertically move in the casing, said biasing means being interposed between the spring holders of the moving units and the casing;

perforating roller means having a polurality of perforating needles on its outer surface and a center rotating shaft, said roller means being seated on the opposed steps of the casing and rotatably supported, at the opposed side ends of the center rotating shaft, by the bearing bodies of the moving units such that the roller means partially projects out of the bottom of the casing; and means for sensing and displaying vertical movement of said moving units, said sensing an displaying menas being placed in said top chamber of the casing.

According to a sixth embodiment of the present invention, there is provided a perforating device for dermal administration comprising:

a casing having opposed steps in its opposed bottom sides and a partition for dividing the inside of the casing into top and bottom chambers, said partition having a pair of holes;

a pair of moving units received in said bottom chamber of the casing such that the moving units are elastically vertically movable in the casing under the guide of the holes of the partition, each of said moving units having a spring holder and a bearing body;

mains for biasing the moving units to make the moving units elastically vertically move in the casing, said biasing means being interposed between the spring holders of the moving units and the casing;

perforating roller means having a plurality of perforating needles on its outer ourface and a center rotating shaft, said roller means being seated on the opposed steps of the casing and rotatably supported, at the opposed side ends of the center rotating shaft, by the bearing bodies of the moving units such that the roller means partially projects out of the bottom of the casing;

means for sensing and displaying vertical movement of said moving units, said sensing and displaying means being placed in said top chamber of the casing; and means for giving an alarm of excessive pressure applied to said perforating roller means.

In the above embodiment, it is desirable that the alarm means generates a visual alarm signal and/or a voice alarm signal.

BRIEF DESCRIPTION OF THE DRAWINGS

The above and other objects, features and other advantages of the present invention will be more clearly understood from the following detailed description taken in conjunction with the accompanying drawings, in which.

DESCRIPTION OF THE PREFERRED EMBODIMENTS

Figure 1:
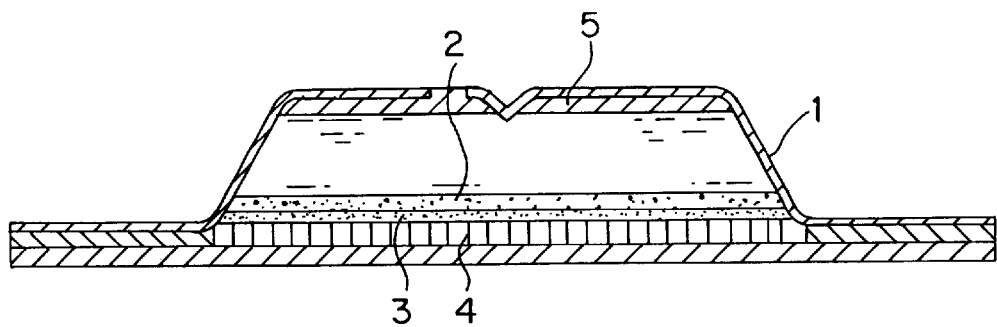
FIG. 1 is a side view showing a construction of a typical patch type instrument for dermal administration of insulin.
Figure 2:
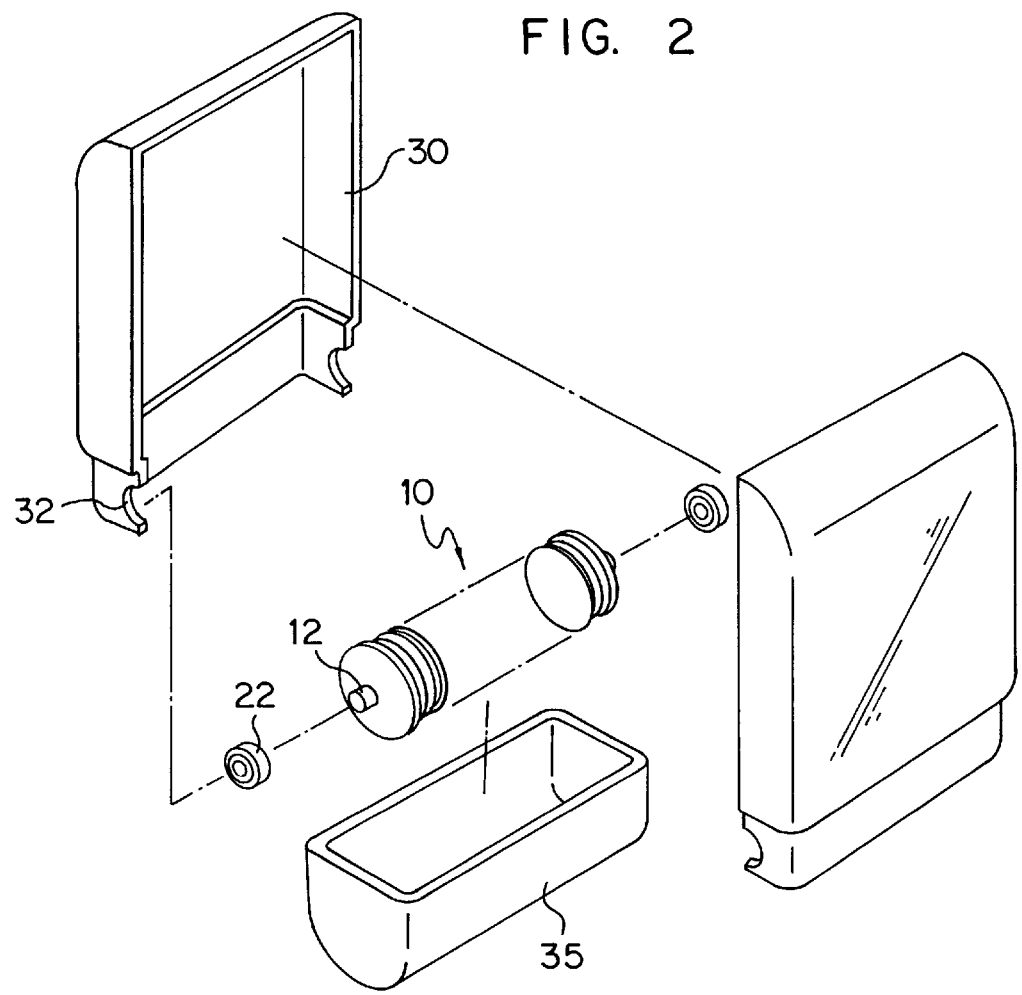
FIG. 2 is an exploded perspective view of a perforating device for dermal administration in accordance with a first embodiment of the present invention.

FIG. 2 is an exploded perspective view of a perforating device for dermal administration in accordance with a first embodiment of the present invention. As shown in this drawing, the perforating device includes skin perforating members 10 which are rotatably placed in the lower section of a casing 30. Otherwise stated, opposed ends of a rotating shaft 12 of the members 10 are received and rotatably held in a bearing 22 engaged with shaft holes 32 of the casing 30.

Figure 3:
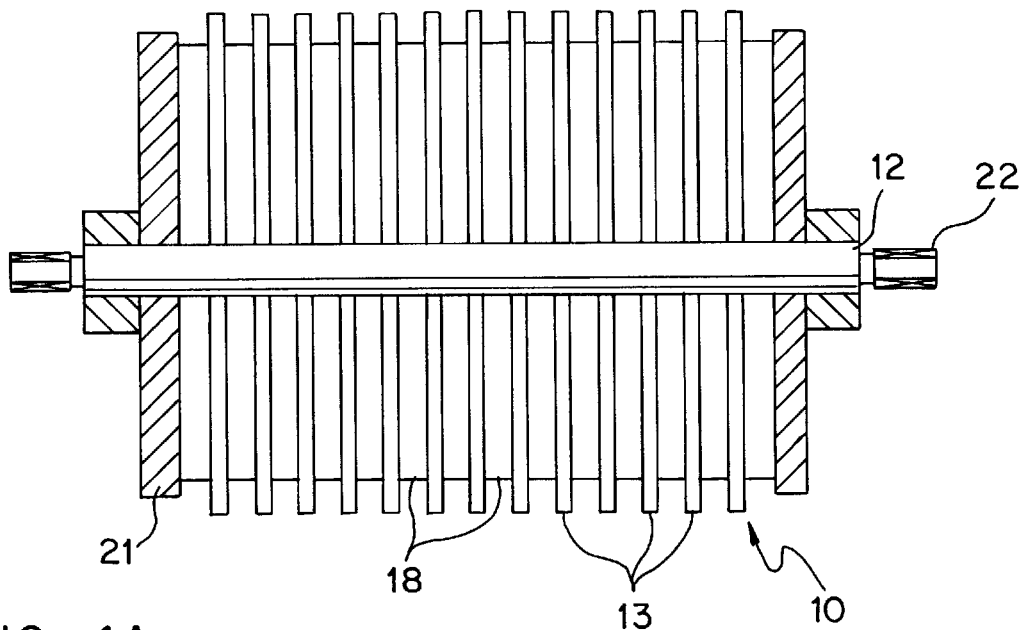
FIG. 3 is an enlarged sectional view of a skin perforating members of the perforating device of FIG. 2.
Figure 4A:
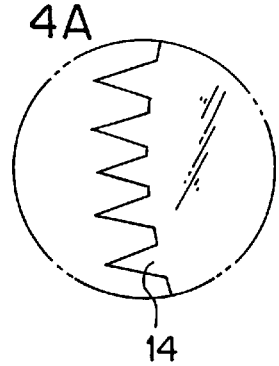
FIGS. 4 and 4A are an enlarged exploded perspective view showing a needle disc, a spacer disc and a reinforcing disc of the skin perforating members of FIG. 3.
Figure 4:
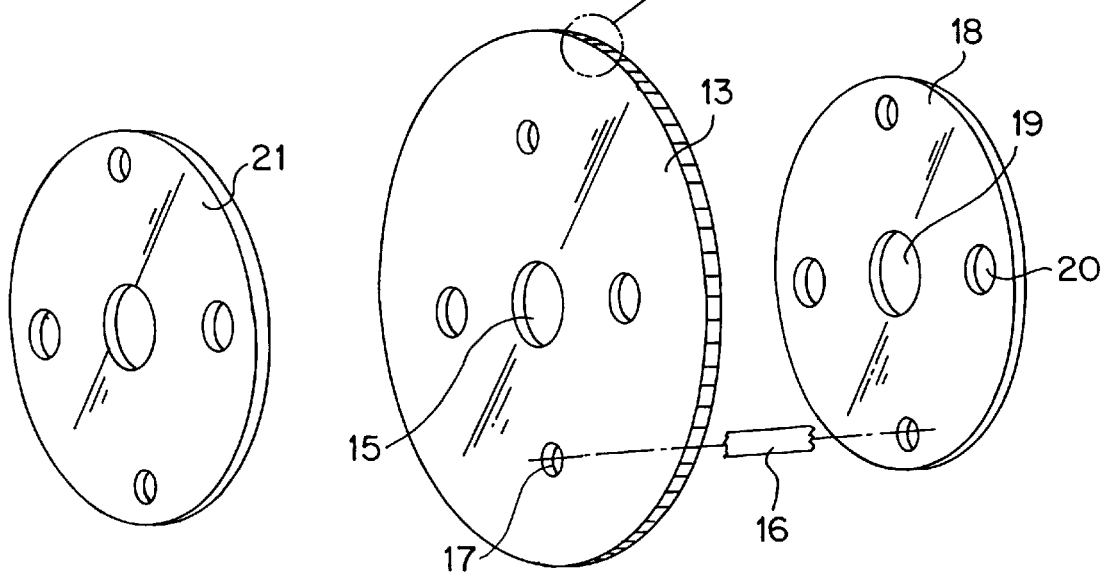
Figure 5:
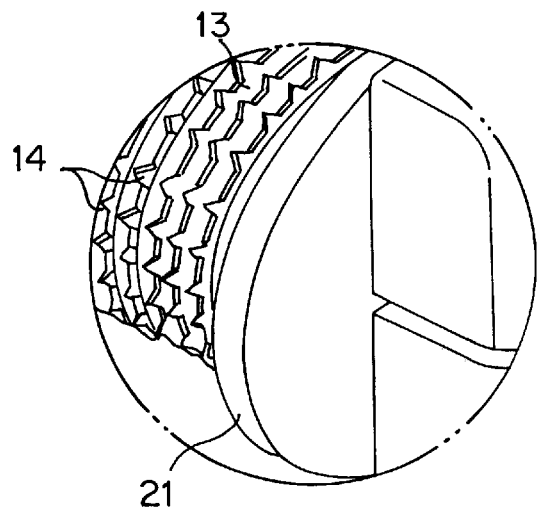
FIG. 5 is a partially enlarged perspective view of the skin perforating members of FIG. 2.
Figure 6:
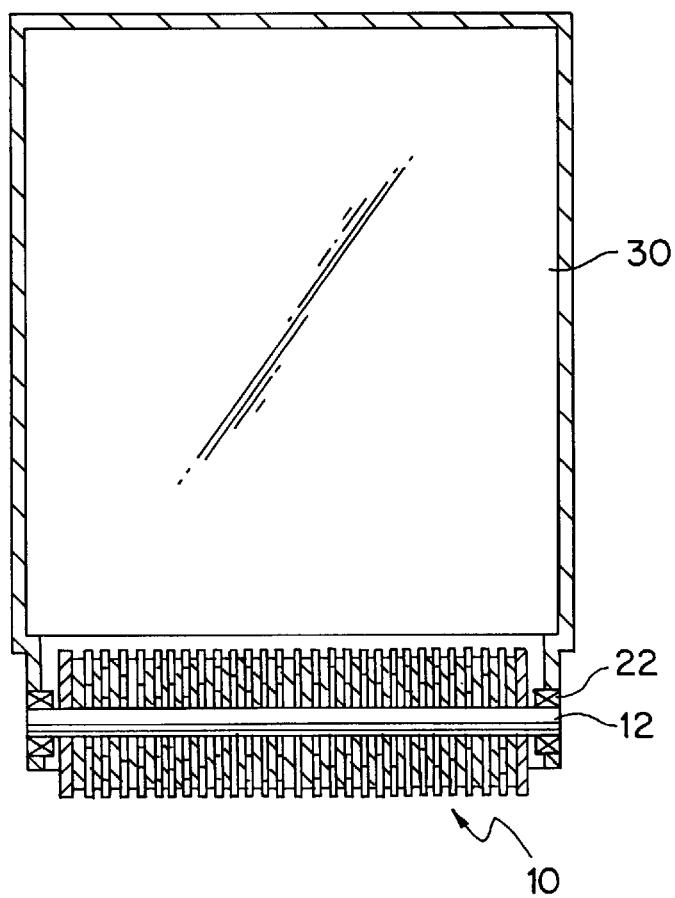
FIG. 6 is a sectional view of the assembled perforating device of FIG. 2.

FIG. 3 is an enlarged sectional view of the skin perforating members 10. FIG. 4 is an enlarged exploded perspective view showing a needle disc 13, a spacer disc 18 and a reinforcing disc 21 of the skin perforating members 10. FIG. 5 is a partially enlarged perspective view of the skin perforating members 10, and FIG. 6 is a sectional view of the assembled perforating device of FIG. 2. As shown in the drawings, each needle disc 13 is a thin disc provided with tens or hundreds of needles 14 on its outer edge. The needles 14 are formed on the edge of the disc 13 through etching or pressing. The disc 13 is also provided with a center shaft hole 15 for receiving a rotating shaft 12. A plurality of fixing holes 17 for receiving their associated fixing rods (not illustrated) are regularly formed in each disc 13 about the shaft hole 15.

The spacer discs 18 interposed between the needle discs 13 are for spacing out the needle discs 13 at regular intervals. Each spacer disc 18 is provided with a center shaft hole 19 and a plurality of fixing holes 20 in the same manner as described for the hole 15 and the holes 17 of each needle disc 13. Of course, it should be understood that each spacer disc 18 may be integrated with an associated needle disc 13 into a single body.

In the skin perforating members 10, the needle discs 13 and the spacer discs 18 are alternatively arranged in this state, the fixing rods pass through the fixing holes 17 and 20 of the discs 13 and 18. The opposed sides of the members 10 are tightened by the reinforcing discs 21. The rotating shaft 12 passes through the shaft holes 15 of the needle discs 13 and through the shaft holes 19 of the spacer discs 18 such that the needle discs 13 can be rotated.

The opposed ends of the shaft 12 are fitted with bearings 22 which in turn are fitted into the shaft holes 32 of the casing 30.

In assembling the above perforating device, the needle discs 13 and the spacer discs 18 are alternately arranged such that their shaft holes 15 and 19 are aligned with each other and their fixing holes 17 and 20 are aligned with each other. Thereafter, the fixing rods are fitted into the aligned fixing holes 17 and 20 of the discs 13 and is and the rotating shaft 12 is fitted into the aligned shaft holes 15 and 19 of the discs 13 and 18. After assembling the elements into the skin perforating members 10, the members 10 are set in the lower section of the casing 30 by fitting the bearings 22 of the shaft 12 into the shaft holes 32 of the casing 30.

In the Skin perforating operation of the above device, the device is brought into contact with the skin to be perforated while gripping the casing 30. The needles 14 of the members 10 thus come into contact with the skin. The members 10 of the device are, thereafter, rolled on the skin while evenly pressing down the device on the skin with a constant pressure.

When rolling the members 10 on the skin with the constant pressure, the needle discs 13 are rotated and perforate the skin and thereby forming the desired number of perforations of a given depth in the skin by the needles 14. After forming the perforations in the skin, the skin is applied with an insulin patch so that insulin in the form of gel medicine, for example, infiltrates the skin through the perforations and is easily transferred to the capillary vessels and thereby achieving the insulin administration through the skin.

Figure 7:
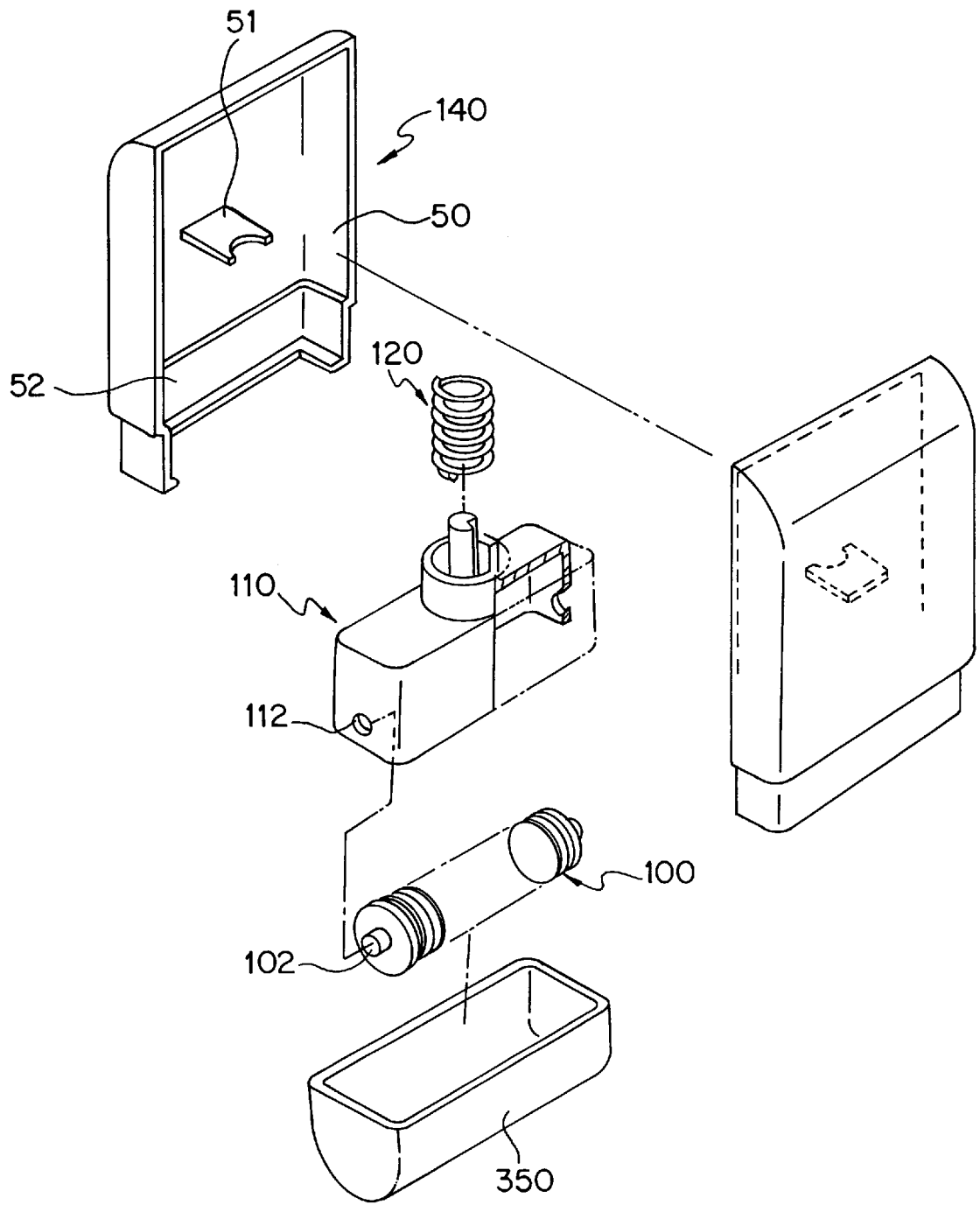
FIG. 7 is an exploded perspective view of a perforating device for dermal administration in accordance with a second embodiment of the present invention.

Turning to FIG. 7, there is shown a perforating device for dermal administration in accordance with a second embodiment of the present invention. In the second embodiment, the skin perforating members 100 have the same construction as that of the firs embodiment and further explanation of the members 100 is thus not deemed necessary.

The skin perforating members 100 are rotatably placed under a moving unit 110. The casing 140 has a recess space 50 therein. Steps 52 are prepared on both bottom sides of the casing 140.

As shown in FIG. 7, inside and outside spring holders, which receive and hold a biasing member 120 such as a coil spring or a plate spring, are integrally equipped in the recess space 50 of the casing 140. A part of the biasing member 120, assembled with the inside and outside spring holder, is placed and held an a supporter 51.

Figure 8:
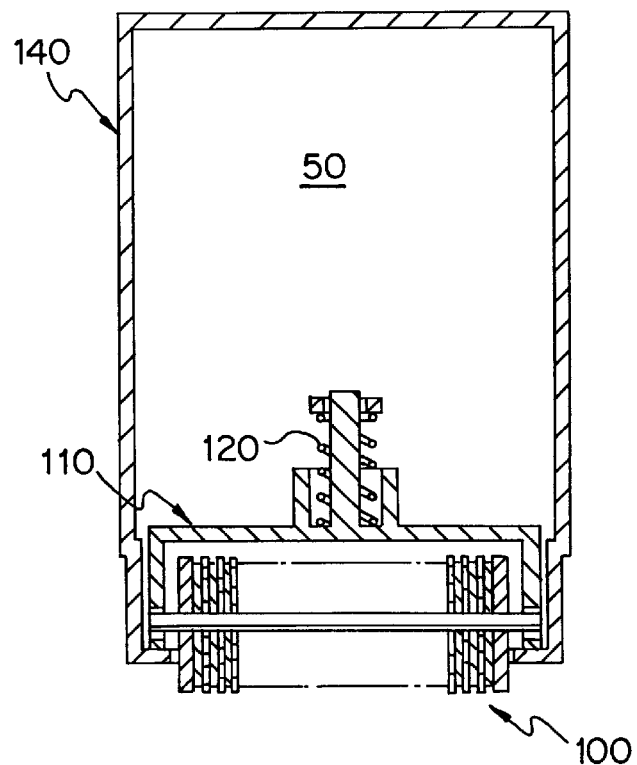
FIG. 8 is a sectional view of the assembled perforating device of FIG. 7.

In the above structure, referring to FIG. 8, the skin perforating members 100 equipped in the recess space 50 of the casing 140 can perforate skin in a regular depth, by moving up and down with the help of the moving unit 110 and biasing member 120.

Figure 9:
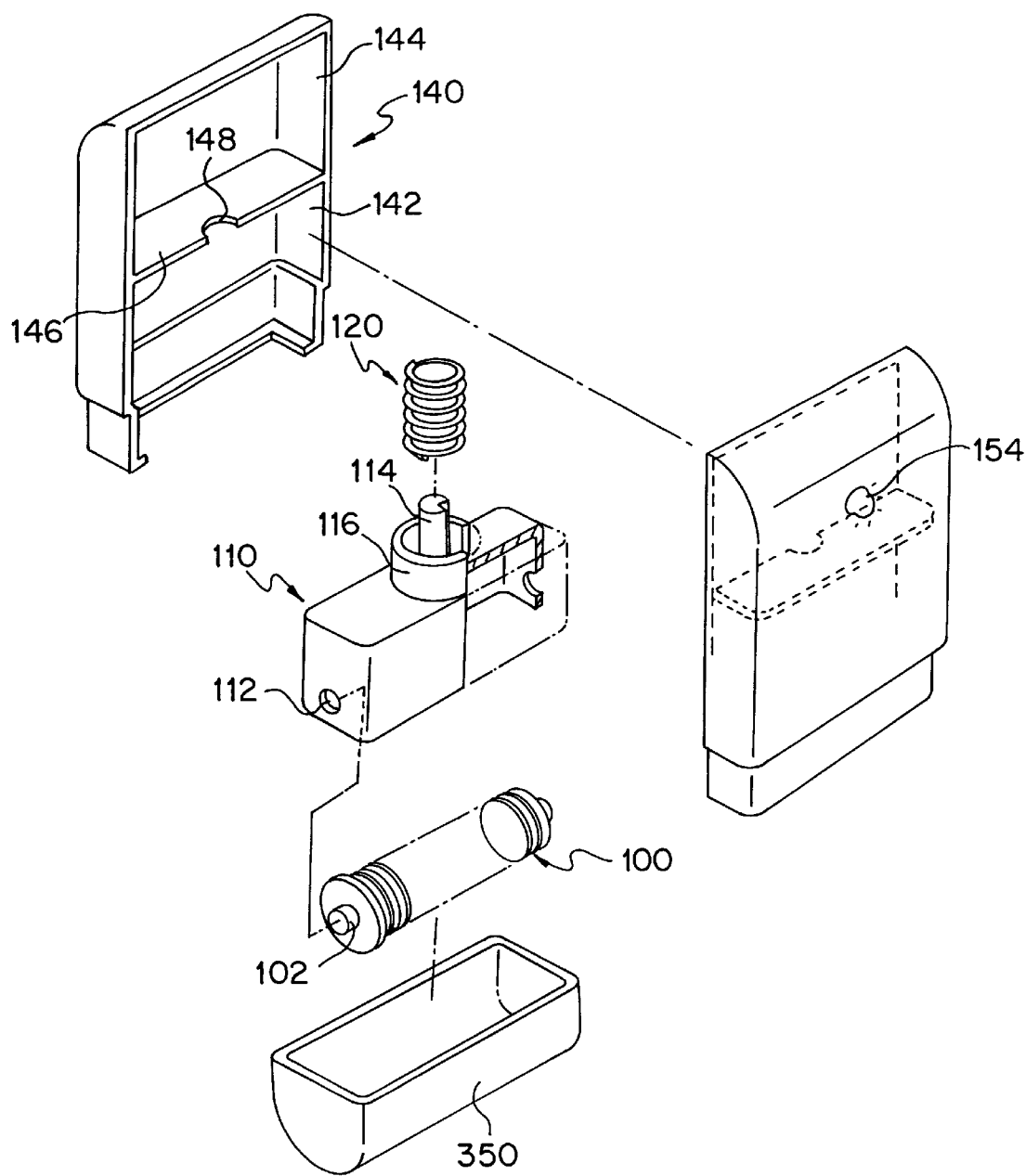
FIG. 9 is an exploded perspective view of a perforating device for dermal administration in accordance with a third embodiment of the present invention.

In FIG. 9, there is shown a perforating device for dermal administration in accordance with a third embodiment of the present invention. In this embodiment, the skin perforating members 100 have the same construction as that of the embodiment of FIG. 2 and further explanation for the members 100 is thus not deemed necessary.

The skin perforating members 100 are rotatably placed under a moving unit 110. Otherwise stated, a rotating shaft 102 of the assembly 100 is received in and rotatively held by shaft holes 112 of the moving unit 110.

As shown in FIG. 9, inside and outside spring holders 114 and 116, which receive and hold a biasing member 120 such as a coil spring or a plate spring, integrally extend from the top of the moving unit 110. The one end of the bottom end of the biasing member 120 is placed and held between the inside and outside spring holders 114 and 116, while the other end of the top end of the member 120 is held by the casing 140.

The casing 140 includes a first chamber 142 for receiving the moving unit 110 and a second chamber 144 for receiving an insulin patch drive unit which comprises, for example, a printed circuit board (PCB), a battery, a switch and a light emitting diode (LED). The first and second chambers 142 and 144 are separated from each other by a horizontally extending partition 146. The partition 146 is provides with a center through hole 148 which movably receives the inside holder 114 of the moving unit 110 and allows upward and downward movement of the holder 114.

Figure 10:
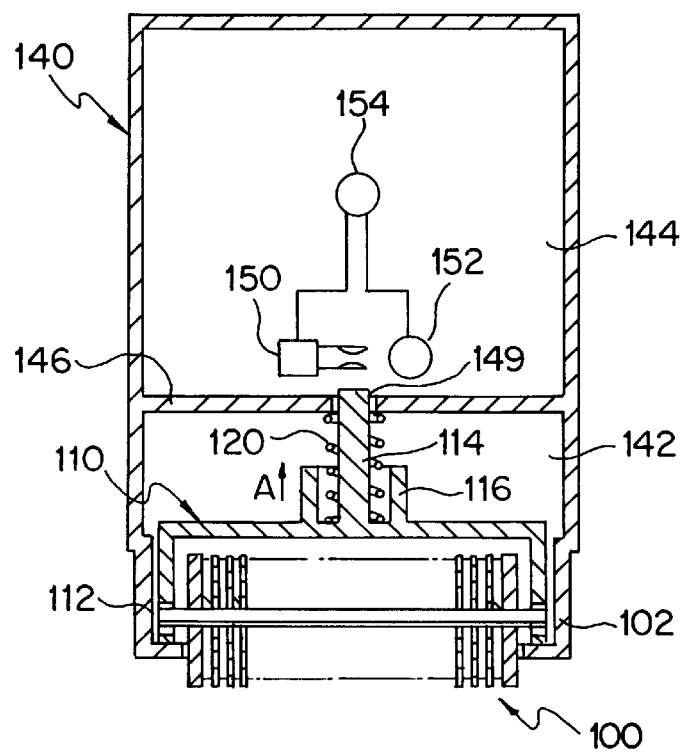
FIG. 10 is a sectional view of the assembled perforating device of FIG. 9.

FIG. 10 is a sectional view of the assembled perforating device of the third embodiment. As shown in the drawing, an insulin patch driving switch 150, a power battery 152 and an LED 154 are placed in the second chamber 144. In addition, a PCB (not shown) is placed in the second chamber 144. In FIG. 10, the reference numeral 149 denotes a step for prevention of possible separation of the moving unit 110 from its position in the casing 140.

In skin perforating operation of the above device according to this embodiment, the device is brought into contact with the skin to be perforated while gripping the casing 140. The casing 140 is, thereafter, pressed down on the skin. The skin perforating members 100 thus comes into contact with the skin and, in this state, the skin perforating members 100 along with the moving unit 110 moves upward as shown at the arrow A of FIG. 10.

When the moving unit 110 moves upward as described above, the inside holder 114 of the unit 110 is lifted up through the hole 148 of the partition 146 so that the top of the holder 116 operates the switch 150. The switch 150 thus turns on the LED 154 so that the LED 154 informs the user of an appropriate perforating pressure applied on the skin perforating members 100.

After perforating the skin using the device, the pressing force is removed from the casing 140 so that the moving unit 110 elastically returns, due to restoring force of the biasing member 120, to its original position in the direction opposed to the arrow A of FIG. 10. That is, the moving unit 110 elastically moves down to its original position. Therefore, the switch 150 is turned off so that the LED 154 is also turned off. The LED 154 in this case informs the user that the members 100 are not perforating the skin any longer.

The perforating device of the second and third embodiment are provided with means, comprising the moving unit 110, the switch 150 and the LED 154, for informing the user of the pressure applied on the skin perforating members 100. Due to the pressure informing means, this device can perforate the skin with constant pressure.

Figure 11:
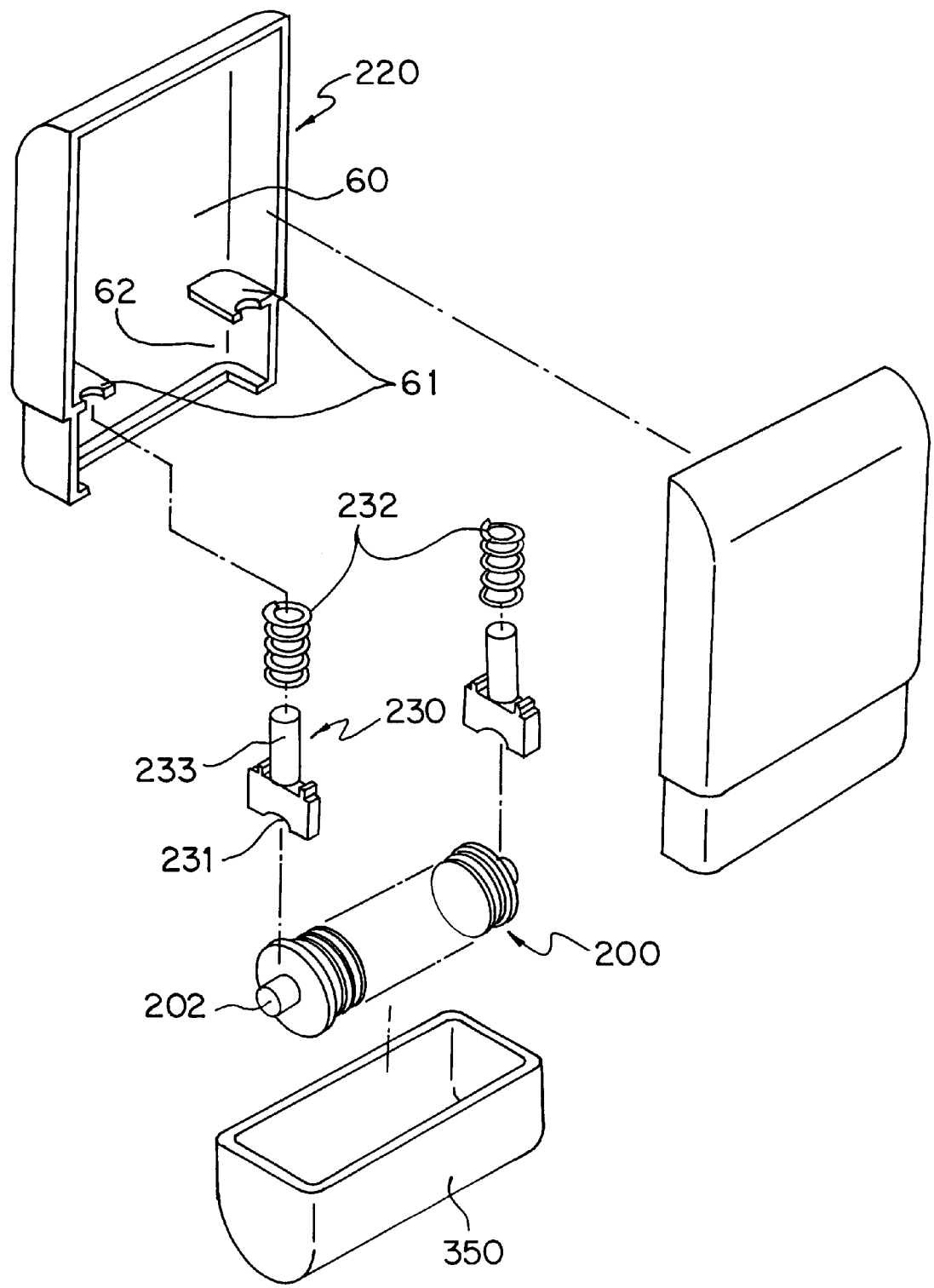
FIG. 11 is an exploded perspective view of a perforating device for dermal administration in accordance with a fourth embodiment of the present invention.

In FIG. 11, there is shown a perforating device for dermal administration in accordance with a fourth embodiment of the present invention. In this embodiment, the skin perforating members 200 has the same construction as that of the first or second embodiment and further explanation for the assembly 200 is thus not deemed necessary.

A central shaft 202 of the skin perforating members 200 is placed on a step 62 of a casing 220, together with a pair of moving units 230. The respective moving units 230 has a fixing rod 233 and a contact face 231. At this time, a pair of biasing members 232 is inserted in the fixing rod 233 and supported elastically by a supporter 61 prepared on the outer side of the casing 220.

Figure 12:
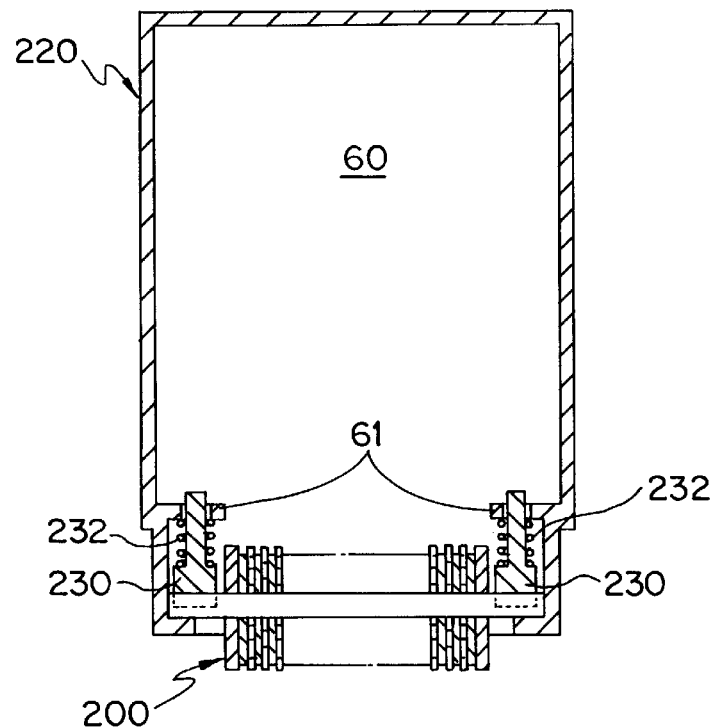
FIG. 12 is a sectional view of the assembled perforating device of FIG. 11.

In the above structure, referring to FIG. 12, the skin perforating members 200 equipped in a recess space 60 of the casing 220 can perforate a skin more regularly than that of the second embodiment, by moving up and down evenly with the help of the moving units 230 and biasing member 232.

Figure 13:
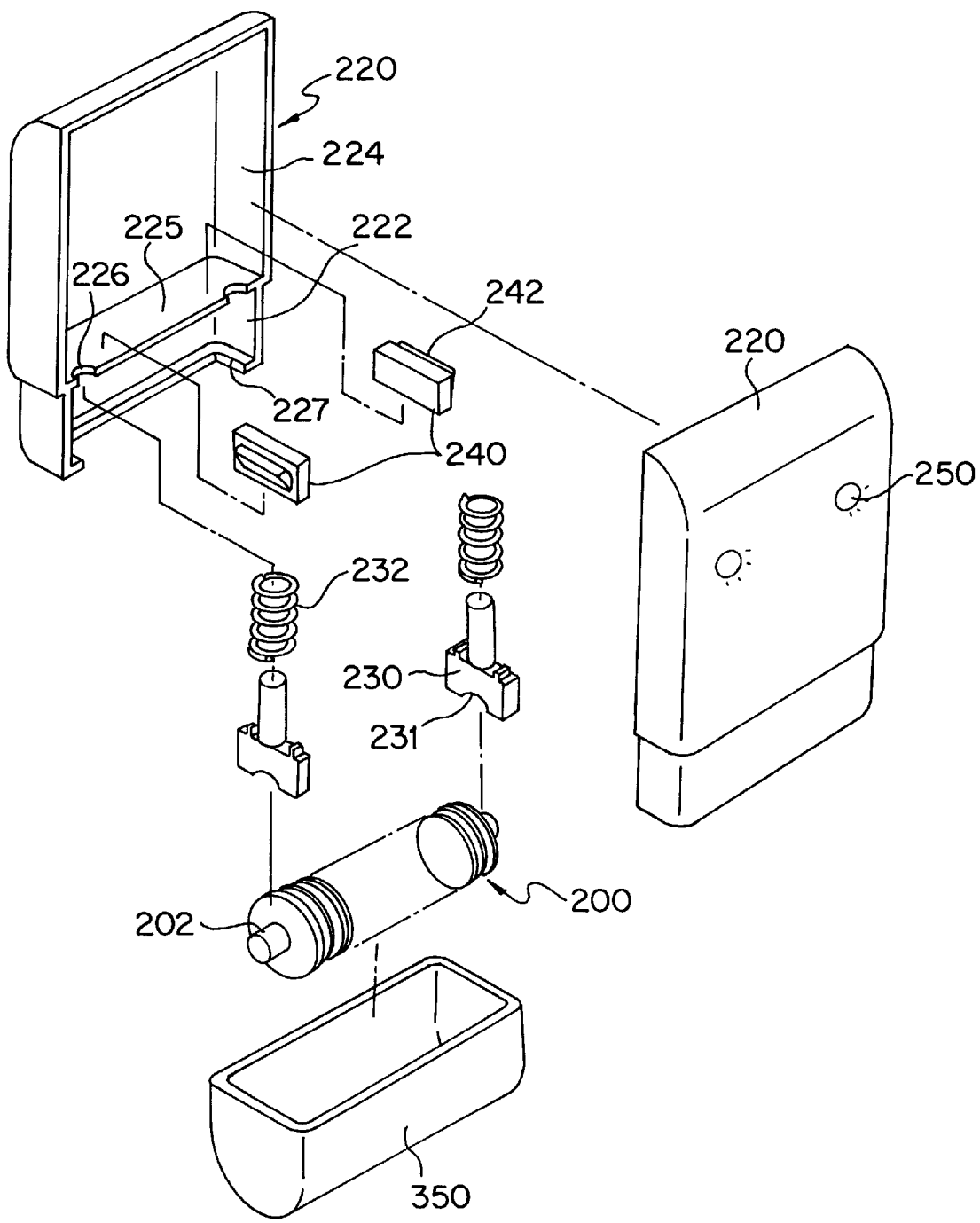
FIG. 13 is an exploded perspective view of a perforating device for dermal administration in accordance with a fifth embodiment of the present invention.

In FIG. 13, there is shown a perforating device for dermal administration in accordance with a fifth embodiment of the present invention. In this embodiment, the skin perforating members 200 has the same construction as that of the first or second embodiment and further explanation for the assembly 200 is thus not deemed necessary.

The skin perforating members 200 is placed in the lower section of a casing 220, the casing 220 also having a drive means. The inside of the casing 220 is generally partitioned into two chambers, that is, a first chamber 222 and a second chamber 224, by a horizontally extending partition 225. The first chamber 222 receives the skin perforating members 200 and a pair of moving units 230, the units 230 being described in detail below.

Each moving unit 230 has a shape which is suitable for sitting on the rotating shaft 202 of the skin perforating members 200. Each moving unit 230 also has a semicircular bearing 231 sitting on the rotating shaft 202 as shown in FIG. 13. Each moving unit 230 further includes a spring holder for holding a biasing member 232, such as a coil spring or a plate spring. The bottom ends of the moving units 230 are placed on opposed ends of the rotating shaft 202, while the top ends of the units 230 are movably inserted in holes 226 formed in the partition 225 of the casing 220. In this case, the biasing members 232 are fitted over the spring holders of the moving units 230 and stopped by the partitions 225 at their top ends. The moving units 230 thus elastically move up or down by the spring force of the biasing members 232 and turn on or turn off their associated switches 240 and then turn on or turn off their associated LEDs 250. At this time, the LEDs 250 are applied with electric power from a battery 260 and thereby emit light.

Figure 14:
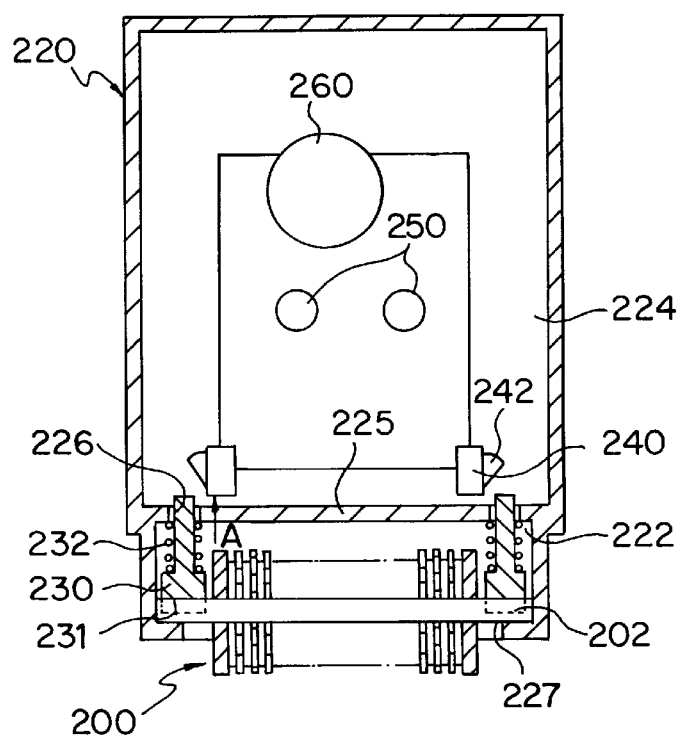
FIG. 14 is a sectional view of the assembled perforating device of FIG. 13.

FIG. 14 is a sectional view of the assembled perforating device of the third embodiment after assembling. As shown in the drawing, the opposed ends of the rotating shaft 202 sit on steps 227 formed in the lower section of the casing 220 so that possible separation of the assembly 200 from its position in the casing 220 can be prevented.

In skin perforating operation of the above device according to the this embodiment, the device is brought into contact with the skin to be perforated while gripping the casing 220. The casing 220 is, thereafter, forcibly pressed down on the skin. The skin perforating members 200 thus comes into contact with the skin and, in this state, the skin perforating members 200 along with the moving units 230 is lifted up as shown at the arrow A of FIG. 14.

When the moving units 230 are evenly lifted up, the spring holders of the units 230 are also lifted up through the holes 226 of the partition 225 so that the tops of the spring holders of the units 230 operate the switches 240. The switches 240 thus turn on the LEDs 250 and this easily informs the user of an appropriate perforating pressure applied on the skin perforating members 200.

After perforating the skin, the pressing force is removed from the casing 220 so that the moving units 230 elastically return, due to the restoring force of the biasing members 232, to their original positions in the direction opposed to the arrow A of FIG. 14. That is, the moving units 230 elastically move down to their original positions. Therefore, the switches 240 are turned off so that the LEDs 250 are also turned off. The LEDs 250 in this case inform the user of that the assembly 200 is not perforating the skin any longer.

During the perforating operation of the above device, the user confirms, through the two LEDs 250, whether the perforating operation is being smoothly and appropriately carried out. When the skin perforating members 200 are not parallel to the skin but inclined to a side, one of the LEDs 250 may be turned off. For example, when the left side of the skin perforating members 200 in the sectional view of FIG. 14 is excessively pressed down, the left switch 240 will be turned on ahead of the right switch 240 and this makes the left LED 250 be turned on ahead of the right LED 250. Therefore, the user can easily adjust the pressing force for the skin perforating members 200 and evenly perforate the skin.

The perforating device of this embodiment is provided with means for checking the pressures applied on opposed ends of the skin perforating members 200 and two LEDs 250 for informing the user of the pressures applied on the opposed ends of the assembly 200. With both the pressure checking means and the LEDs 250, this device lets the user evenly perforate the skin while checking the pressures applied on the opposed ends of the skin perforating members 200.

Figure 15:
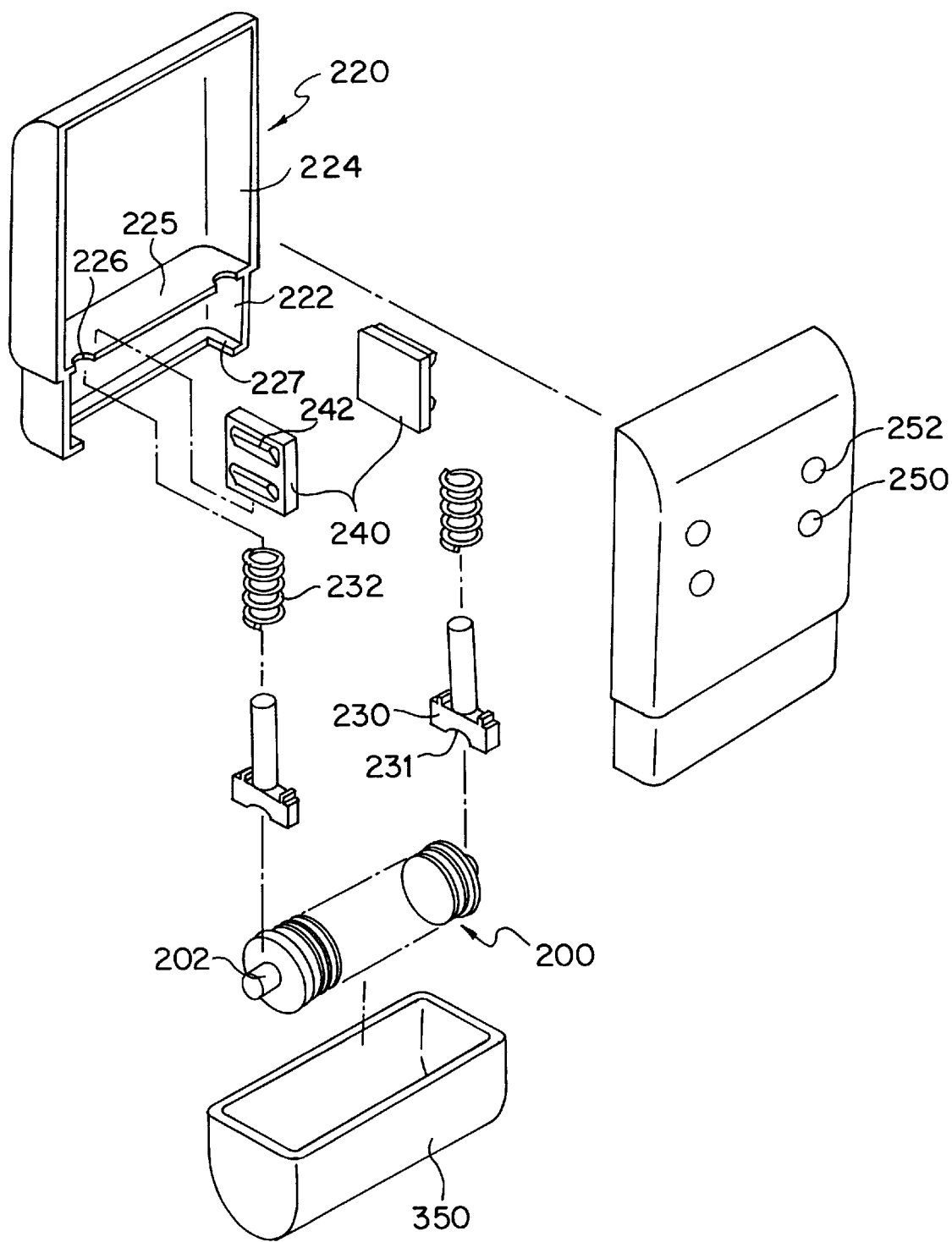
FIG. 15 is an exploded perspective view of a perforating device for dermal administration in accordance with a sixth embodiment of the present invention.

In FIG. 15, there is shown a perforating device for dermal administration in accordance with a sixth embodiment of the present invention. In this embodiment, most of the elements are common with those of the fifth embodiment. Those elements common to both the fourth and fifth embodiments will carry the same numerals and further explanation for the common elements is thus not doomed necessary.

Figure 16:
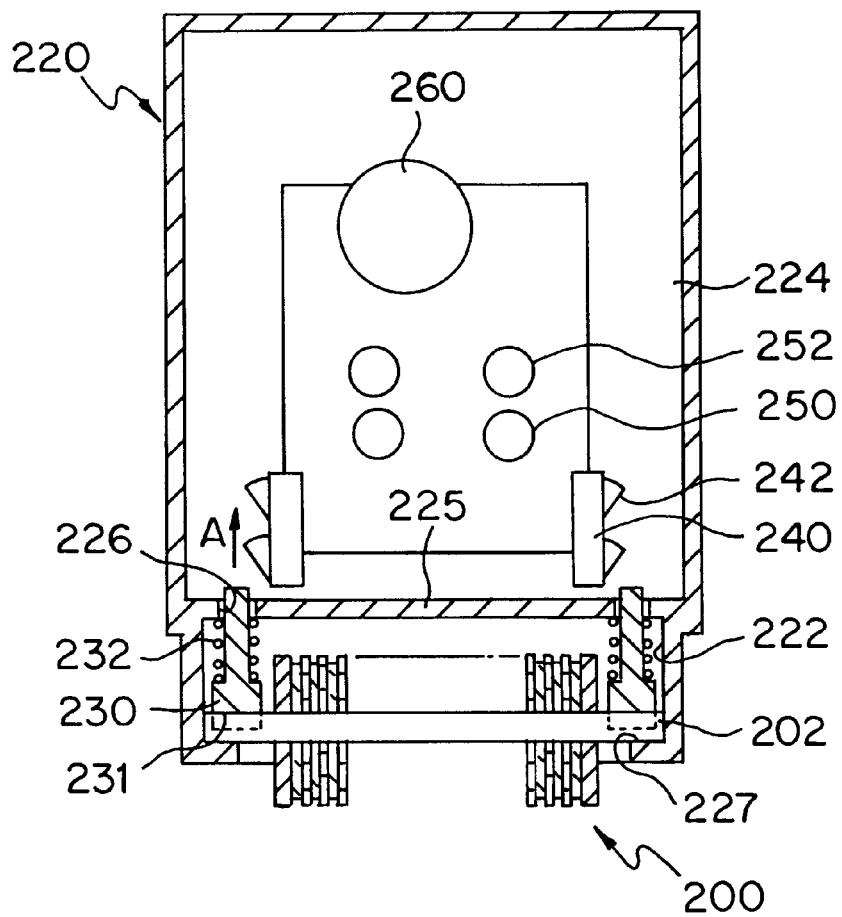
FIG. 16 is a sectional view of the assembled perforating device of FIG. 15.

As shown in FIGS. 15 and 16, the moving units 230 are arranged in the casing 220 such that the units 230 operate their associated first switches or lower switches 240 and their associated second switches or upper switches 242, The lower switches 240 are turned on when the skin perforating members 200 come into contact with the skin with an appropriate pressure, while the upper switches 242 are turned on when the skin perforating members 200 come into contact with the skin with an excessive pressure.

When the device is pressed down on the skin at the appropriate pressure under the condition that the device is brought into contact with the skin, the skin perforating members 200 is elastically lifted up as shown at the arrow A of FIG. 16. In this case, the top ends of the moving units 230 turn on the lower switches 240.

The lower switches 240 thus turn on lower LEDs 250 and thereby informing the user of the skin perforated to a depth suitable for medication by insulin through the skin.

When the moving units 230 is lifted up higher, the upper switches 242 are turned on. The switches 242 thus turn on upper LEDs or alarm LEDs 252 and thereby informing the user of excessive pressure which could possibly cause skin damage, applied on the skin perforating members 200. Of course, it should be understood that the alarm means may use sound alarm devices, such as a buzzer or melody IC, instead of the LEDs 250 and 252. Alternatively, the alarm means may generate a sound alarm signal and a visual alarm signal at the same time.

When the pressing force is removed from the casing 220, the moving units 230 elastically return, due to restoring force of the biasing members 232 such as coil springs or plate springs, to their original positions in the direction opposed to the arrow A of FIG. 16.

The perforating device of this sixth embodiment is provided with means for checking the pressures applied on opposed ends of the skin perforating members 200 and four LEDs 250 and 252 for informing the user of the pressures applied on the assembly 200. LEDs 250 and 252 are supplied with electric power from a battery 260. With both the pressure checking means and the LEDs, this device lets the user easily check whether the perforating operation of the device is carried out with appropriate pressure.

Figure 17:
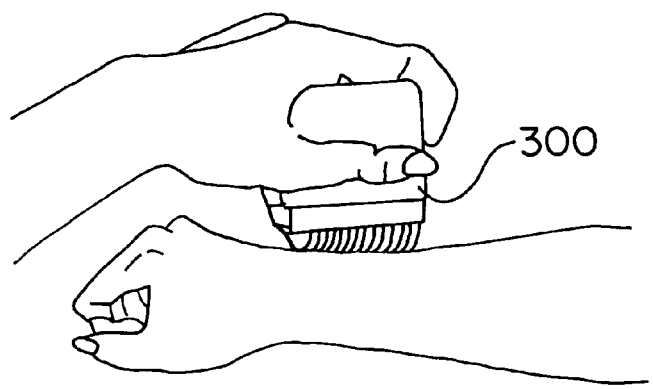
FIG. 17 is a view showing an operation situation of a perforating device for dermal administration in accordance with the present invention.

The first to sixth embodiments so far described will efficiently accomplish their performances in accordance with an operation situation of a skin perforating members depicted in FIG. 17 showing device 300. Meanwhile, a cap 35 or 350 is provided to be put on the skin perforating device for the protection of the device.

As described above, the present invention provides an improved perforating device for dermal administration of medicine. The device includes a skin perforating member which is provided with a plurality of needles and received in a casing. The skin perforating members easily and evenly perforate the skin to a depth suitable for dermal administration of medicine. The device also includes biasing means for preventing the skin perforating members from perforating the skin with excessive pressure. The device also informs the user of the excessive pressure of the assembly and thereby preventing possible skin damage during skin perforation.

Although the preferred embodiments of the present invention have been disclosed for illustrative purposes, those skilled in the art will appreciate that various modifications, additions and substitutions are possible, without departing from the scope and spirit of the invention as disclosed in the accompanying claims.

What is claimed is:

1. A perforating device for dermal administration of a pharmaceutically acceptable composition, comprising:

a casing including a pair of opposing side walls respectively formed with opposed bottom side portions and a shaft hole located in each of said bottom side portions;

a plurality of needle disks having a plurality of skin perforating needles on their circumferential surfaces, wherein the opposing side walls substantially entirely enclose the disks but are open at a bottom thereof through which the skin perforating needles partially project outside the casing;

a central shaft received in each of said shaft holes in said bottom side portions for holding the needle disks assembled therealong in a face-to-face relationship with one another and having opposed side ends;

a plurality of spacers assembled on the central shaft so that each of the spacers is alternately disposed between the needle disks;

a fixing arrangement for fixing and joining the needle disks with the respective spacers to permit rotation of the disks and spacers, said needle disks being rotatably supported by the casing at the opposed side ends of the central shaft.

2. The device of claim 1, wherein said casing substantially entirely encloses the central shaft.

3. The device of claim 2, wherein said needle disks project partially out of a bottom of the casing.

4. The device according to claim 1, wherein bearings are respectively located in each of the shaft holes.

5. The device according to claim 1, wherein outermost ends of the central shaft are supported in the casing.

6. The device of claim 1, wherein each of the skin perforating needles is generally of triangular shape and has saw teeth on its periphery.

7. The device of claim 1, wherein each of said opposing side walls extends longitudinally along the entire length of said shaft and on opposite sides thereof to enclose said needle disks.

8. A perforating device for dermal administration of a pharmaceutically acceptable composition, comprising:

a casing having opposed bottom sides and steps formed in each bottom side and a partition for dividing the inside of the casing into top and bottom chambers, said partition having a pair of holes;

a pair of moving units received in said bottom chamber of the casing such that the moving units are elastically and vertically movable in the casing under the guide of the holes of the partition, each of said moving units having a spring holder and a bearing body;

means for biasing the moving units to make the moving units move elastically and vertically in the casing, said biasing means being interposed between the spring holders of the moving units and the casing;

perforating roller means having a plurality of perforating needles on its outer surface and a center rotating shaft, having opposed side ends said roller means being seated on the opposed steps of the casing and rotatably supported, at the opposed side ends of the center rotating shaft, by the bearing bodies of the moving units such that the roller means partially projects out of the bottom of the casing; and means for sensing and displaying vertical movement of said moving units, said sensing and displaying means being placed in said top chamber of the casing.

9. The device according to claim 8, wherein said sensing and displaying means comprises:

a pair of switching devices acting by contact with said spring holders of said moving unit;

a pair of display devices acting in accordance with said switching devices, respectively;

a power supply for supplying said switching devices and said display devices with a source voltage; and a circuit board for integrating said switching devices, display devices, and power supply.

10. The device according to claim 9, wherein said switching devices are transistors.

11. The device according to claim 9, wherein said display devices are light-emitting diodes.

12. The device according to claim 9, wherein said display devices are melody integrated-circuits.

13. The device according to claim 9, wherein said display devices are buzzers.

14. The device according to claim 8, wherein said biasing means is a coil spring.

15. A perforating device for dermal administration of a pharmaceutically acceptable composition, comprising:

a casing having opposed bottom side portions and a shaft hole located in each of said bottom side portions and having opposed step portions;

a moving unit received in said casing such that it is elastically and vertically movable in the casing, the bottom of said moving unit being seated on the opposed step portions of the casing;

means for biasing the moving unit to make the moving unit move elastically and vertically in the casing, said biasing means being interposed between the moving unit and the casing; and perforating roller means having a plurality of perforating needles on an outer surface thereof and a center rotating shaft having opposed ends, said roller means being rotatably supported at the opposed ends of the center rotating shaft by the moving unit such that the roller means partially projects out of the bottom of the casing.

16. A perforating device for dermal administration of a pharmaceutically acceptable composition, comprising:

a casing having opposed bottom side portions and opposed step portions respectively formed in said bottom side portions;

a moving unit elastically and vertically movably received in the casing, a bottom of said moving unit being seated on the opposed step portions of the casing;

a biasing member arranged to bias the moving unit to make it move elastically and vertically in the casing, said biasing member being interposed between the moving unit and the casing; and a plurality of perforating rollers having a plurality of perforating needles on an outer surface thereof and a center rotating shaft having opposed ends, said rollers being rotatably supported at the opposed ends of the center rotating shaft by the moving unit such that the rollers partially project out of the bottom of the casing.

* * * * *